(12) United States Patent
Magana

(10) Patent No.: US 8,366,664 B2
(45) Date of Patent: *Feb. 5, 2013

(54) AGENT DELIVERY CATHETER HAVING ARTICULATING ARMS

(75) Inventor: Jesus Magana, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/236,392

(22) Filed: Sep. 19, 2011

(65) Prior Publication Data

US 2012/0041375 A1    Feb. 16, 2012

Related U.S. Application Data

(62) Division of application No. 12/327,975, filed on Dec. 4, 2008, now Pat. No. 8,021,332.

(51) Int. Cl.
*A61M 29/00* (2006.01)

(52) U.S. Cl. ........................ 604/106; 604/104

(58) Field of Classification Search ............... 604/96.01, 604/101.01, 101.03, 105–109; 606/200, 606/191; 623/1.1, 1.11; 600/204
See application file for complete search history.

(56) References Cited

U.S. PATENT DOCUMENTS

| 6,071,263 | A  | * | 6/2000 | Kirkman | 604/104 |
| 7,431,729 | B2 | * | 10/2008 | Chanduszko | 606/213 |
| 7,470,252 | B2 | * | 12/2008 | Mickley et al. | 604/103.02 |
| 2005/0203462 | A1 | * | 9/2005 | Katoh et al. | 604/164.1 |

* cited by examiner

*Primary Examiner* — Christopher D Koharski
(74) *Attorney, Agent, or Firm* — Fulwider Patton LLP

(57) ABSTRACT

An agent delivery catheter which has a support member comprising at least one articulating arm having an end fixedly secured relative to the shaft and having an anchor end section opposite to the fixed end. The articulating arm is biased to pivot at the fixed end away from the shaft, to transform from a low profile configuration to a high profile configuration in which the arm extends laterally away from the shaft and the anchor end section contacts the patient's body lumen wall, to support the shaft in the body lumen during delivery of an agent, for example by injection from a needle extended from the catheter into the wall of the body lumen.

16 Claims, 5 Drawing Sheets

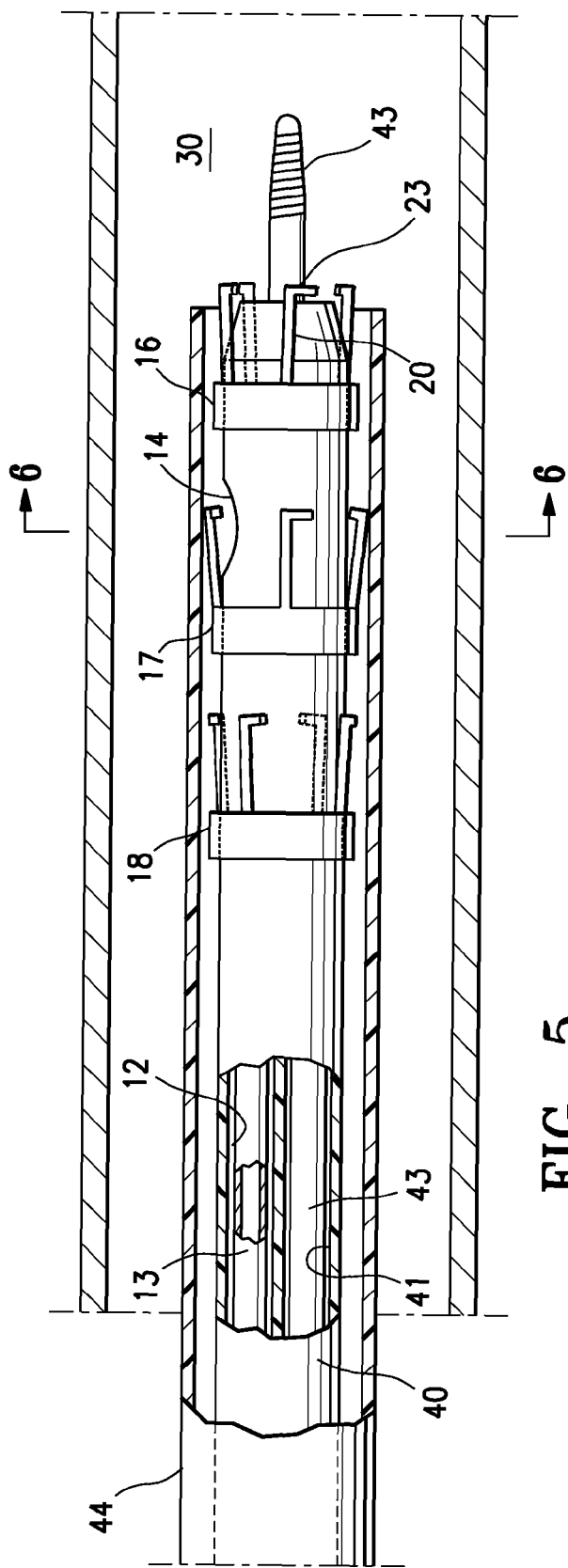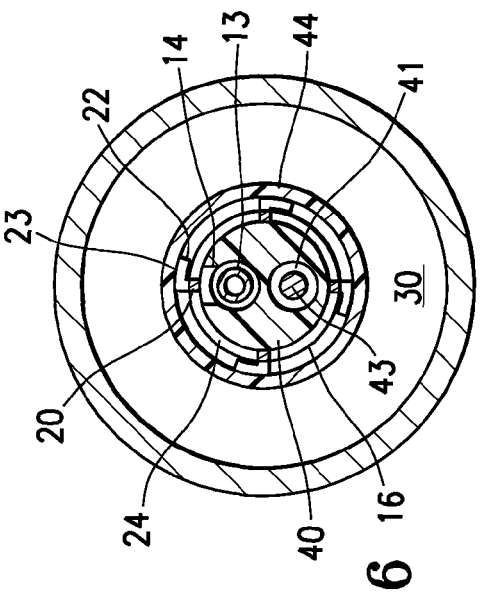
FIG. 5
FIG. 6

AGENT DELIVERY CATHETER HAVING ARTICULATING ARMS

CROSS-REFERENCES TO RELATED APPLICATIONS

This application is a divisional of U.S. Ser. No. 12/327,975, filed on Dec. 4, 2008, issuing on Sep. 20, 2011 as U.S. Pat. No. 8,021,332.

BACKGROUND OF THE INVENTION

The invention relates to the field of medical devices, and more particularly to catheters, such as needle catheters or other elongated devices configured for inserting into a patient's body lumen to perform a diagnostic or therapeutic procedure, such as delivery of an agent to the coronary or peripheral vasculature.

The delivery of therapeutic agents into various parts of the vascular system has been shown to be an effective method of treating vascular disease. A variety of agents can be delivered including anti-proliferative, anti-inflammatory, anti-neoplastic, anti-platelet, anti-coagulant, anti-fibrin, anti-thrombotic, anti-mitotic, antibiotic, anti-allergic, and antioxidant compounds. To treat a diseased section of the vessel, these agents could be delivered directly into the vessel wall adjacent to the diseased section, and/or into the periadventitial (perivascular) space. Vascular regenerative therapies, such as the delivery of mesenchymal stem cells, require the delivery of a bolus of biologic materials into a portion of the vascular system such as into the tissue surrounding a coronary vessel. Local, as opposed to systemic delivery is a preferred method of treatment in that smaller total levels of medication are administered in comparison to systemic dosages yet are concentrated at a specific site. As a result, local delivery produces fewer side effects and achieves more effective results.

A variety of methods and devices have been proposed for percutaneous drug delivery to a diseased region of the vasculature, including catheters having a needle configured to be directed out of the catheter and into the vessel wall to deliver the desired agent to the tissue. In order to properly position the distal end of a drug delivery catheter in a patient's tortuous distal vasculature, the catheter should preferably have a low-profile, flexible distal section despite also having the necessary structural components required for the drug delivery at the operative distal end of the catheter. However, these are often competing considerations, making it difficult to provide the necessary operative distal end while still having good deliverability (i.e., ability to track within the patient's vasculature to a desired location therein).

SUMMARY OF THE INVENTION

The invention is directed to an agent delivery catheter which has a support member comprising at least one articulating arm having an end fixedly secured relative to the shaft and having an anchor end section opposite to the fixed end. The articulating arm is biased to pivot at the fixed end away from the shaft, to transform from a low profile configuration to a high profile configuration in which the arm extends laterally away from the shaft and the anchor end section contacts the patient's body lumen wall, to support the shaft in the body lumen during delivery of an agent.

In a presently preferred embodiment, the catheter is a needle catheter generally comprising an elongated shaft having a proximal end, a distal end, a needle-through lumen slidably containing a needle therein, and at least one needle-through port in a distal shaft section such that the needle has a retracted and an extended configuration, and the articulating arm support member is secured to the shaft at a location adjacent to the needle-through port. Preferably, the needle-through port is in a side wall of the distal shaft section for lateral egress of the needle, and the catheter has a proximal support member mounted to the shaft proximally adjacent to the port, and a distal support member mounted to the shaft distally adjacent to the port. Each support member typically has a collar section which mounts the support member to the shaft. In the high profile configuration, the arms of the support members support the shaft in a position spaced away from the body lumen wall at the location of the port. In a presently preferred embodiment, the shaft is supported in a position spaced away from the body lumen wall around the circumference of the shaft, such that the needle slidably exits the needle-through lumen in the extended configuration through the port spaced away from the body lumen wall for injecting an agent into the wall of the patient's body lumen.

The arms are typically configured to reversibly transform from the low to the high profile configuration by the retraction and advancement of an outer sheath. Each support member has at least one articulating arm, or more typically at least two articulating arms circumferentially spaced around the circumference of the shaft. The number of arms determines the force applied to the vessel wall by the support members, such that the force can be decreased or increased by providing fewer or more arms at each support member. Each arm of a support member pivots as an individual unit, not otherwise connected to an adjacent arm, except by being connected to the shaft. As a result, the support members preferably do not disadvantageously increase the stiffness of the distal shaft section. Additionally, the support members provide for perfusion of fluid in the patient's body lumen (i.e., allow blood within the body lumen to flow past the support member in the high profile configuration). More particularly, in one embodiment, the support members provide a relatively large perfusion pathway around an outer surface of the shaft because the relatively small individual arms of the support members obstruct very little of the body lumen in the high profile configuration. Moreover, the configuration of the support members allows the outer sheath profile to be sized to closely match the underlying catheter shaft, so that the catheter has a very low profile configuration which facilitates advancing the catheter within the patient's vasculature.

With the anchor end section of each arm in contact with the inner surface of the patient's body lumen wall, the catheter shaft is well supported in the body lumen at the location of the needle-through port, allowing for accurate delivery of an agent from the needle to a target tissue location in the body lumen. Due to the support members of the invention, the catheter thus has a low profile, flexible distal section, which provides for continuous blood perfusion during delivery and deployment of the catheter, and which is self-centering within the patient's body lumen at a desired injection site. These and other advantages of the invention will become more apparent from the following detailed description of the invention and accompanying exemplary drawings.

BRIEF DESCRIPTION OF THE DRAWINGS

FIG. 5 illustrates the catheter of FIG. 1 with the arms in the low profile configuration.

FIG. 6 is a transverse cross section of FIG. 5, taken along line 6-6.

DETAILED DESCRIPTION OF THE PREFERRED EMBODIMENTS

Figure 1:
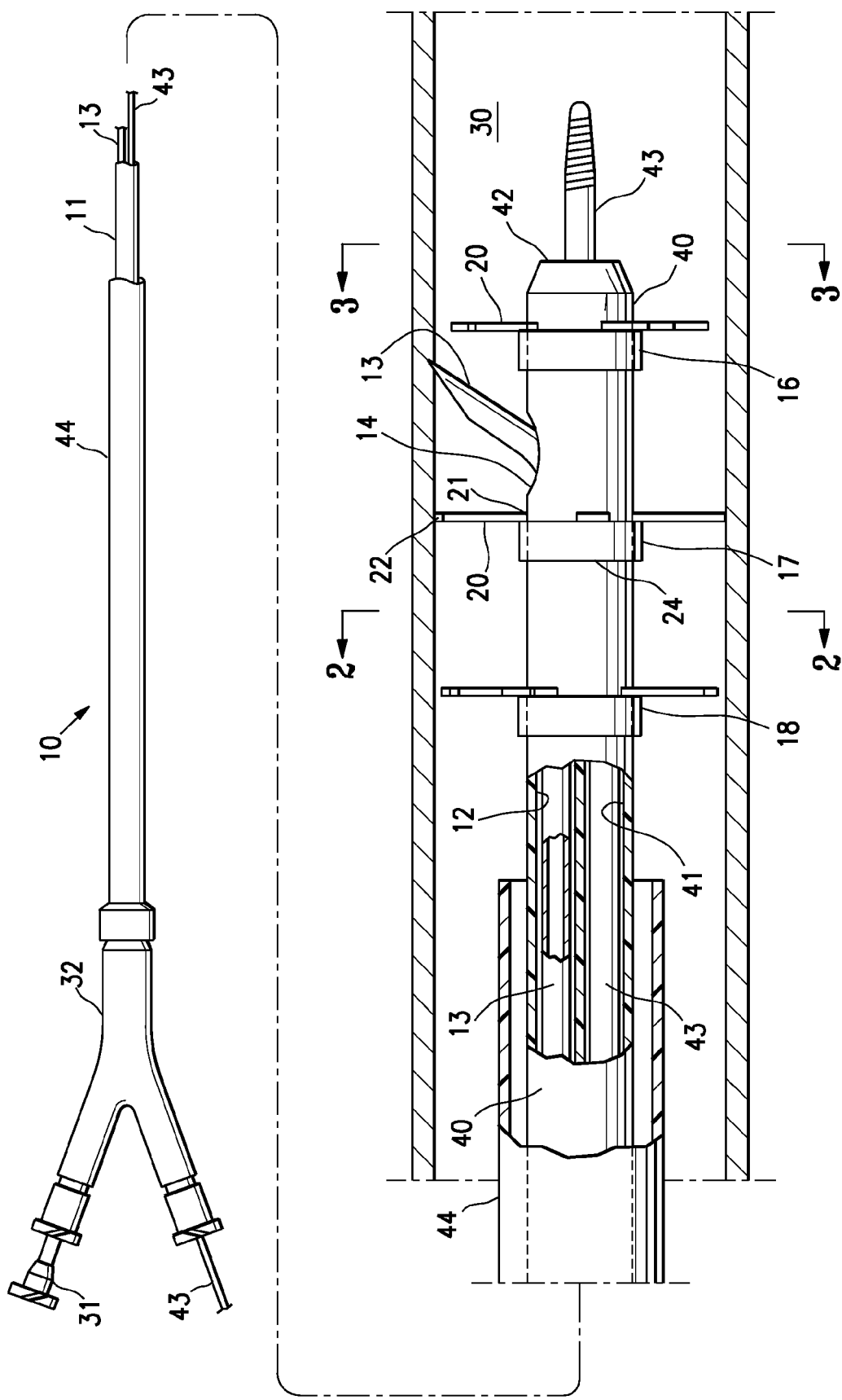
FIG. 1 is an elevational, partially in section, view of an agent delivery perfusion catheter embodying features of the invention, which has proximal and distal support members with articulating arms having a free end bent at a substantially right angle to form an anchor end section of each arm.

FIG. 1 illustrates an elevational, partially in section, view of an agent delivery perfusion catheter 10 embodying features of the invention, generally comprising an elongated catheter shaft 11 having a proximal end, a distal end, a distal shaft section, a needle-through lumen 12 slidably containing a hollow needle 13 therein, and at least one needle-through port 14 in a side of a distal shaft section for lateral egress of the needle 13 such that the needle has an extended and retracted configuration, and a distal support member 16 mounted to the shaft at a first location distally adjacent to the needle-through port 14, and a first proximal support member 17 mounted to the shaft at a second location proximally adjacent to the needle-through port 14, and a second proximal support member 18 mounted to the shaft at a third location proximally adjacent to the first proximal support member 17. The support members comprise articulating arms 20, and each arm 20 has an end 21 fixedly secured relative to the shaft and an opposite end 22 forming an anchor end section 23 (see FIGS. 2-4), and is biased to pivot at the fixed end 21 away from the shaft 11 to transform from a low profile configuration to a high profile configuration in which the arm 20 extends laterally away from the shaft 11. FIG. 1 illustrates the catheter 10 in a patient's body lumen 30, with the support member arms 20 in the high profile configuration such that the anchor end section 23 contacts, without piercing, the patient's body lumen wall to support the shaft 11 proximal and distal to the needle-though port 14 in the body lumen 30. The catheter 10 is configured to be introduced into the patient's vasculature and advanced percutaneously in a low profile configuration illustrated in FIG. 5, with the support member arms 20 in the low profile configuration and the needle 13 distal end retracted within the shaft 11, to position the port 14 at a desired location. The support member arms 20 are then deployed to the high profile configuration and the needle distal end slidably advanced out the port 14 and into the body lumen wall, and agent delivered from the needle to the tissue (e.g., into the vessel wall and/or perivascular space). The needle tip extends radially beyond the outer profile of the arms 20 in the high profile configuration, although the catheter is typically configured to allow the needle 13 to extend only a set limited distance away from the shaft, as for example by providing the catheter 10 with a needle stop member (not shown). FIG. 1 illustrates the needle partially extended in the wall of the body lumen 30. Following an injection, the needle is retracted into the shaft 11 and the support member arms returned to the low profile configuration, to allow the catheter 10 to be repositioned or removed from the body lumen 30 at the end of the agent delivery procedure.

In embodiment illustrated in FIG. 1, the shaft 11 comprises a dual-lumen extrusion tubular member 40 having the needle-though lumen 12 and port 14 therein, and further having a guidewire lumen 41 therein that is eccentrically located relative to the needle-through lumen 12 and extends to a distal port 42 in the distal end of the catheter 10. However, a variety of suitable shaft designs can be used as discussed in more detail below. A handle 31 at the proximal end of the needle 13 is configured for attaching to an agent source (not shown) to flow agent through the lumen of the needle 13 to the piercing distal tip of the needle 13. A proximal adapter 32 secured to the shaft proximal end provides access to the needle-through lumen 12, and, in the embodiment of FIG. 1, also provides access to the guidewire lumen 41. A guidewire 43 is slidably disposed in the guidewire lumen 41. Although the guidewire lumen 41 illustrated in FIG. 1 extends to the proximal end of the catheter 10, the catheter can alternatively or additionally be configured for rapid exchange as is generally known, such that a guidewire proximal port is provided distally spaced from the shaft proximal end in a sidewall of the shaft 11 in communication with the guidewire lumen 41.

In the illustrated embodiment, the support member arms are biased to assume the high profile configuration in a relaxed state, such that the support member arms are self-expanding, and an outer sheath 44 slidably disposed on the catheter shaft 11 is used to restrain the arms 20 in the low profile configuration. The outer sheath 44 has an advanced configuration in which it surrounds and thereby collapses the arms 20 (see FIG. 5) and a retracted configuration in which the distal end of the outer sheath 44 is proximally spaced from the deployed support member arms 20 as illustrated in FIG. 1. The outer sheath 44 can be used to deliver the catheter 10 by advancing together with the catheter 10 positioned therein to the target injection site, or by first positioning the outer sheath 44 at the target injection site in the body lumen 30 and then slidably advancing the catheter 10 within the outer sheath to the target injection site. Thus, the catheter 10 in one embodiment is configured to be completely removed from the outer sheath 44 prior to the introduction of the outer sheath 44 into the patient's body lumen 30. In alternative embodiments, the catheter 10 and outer sheath 44 are configured to be permanently coaxially disposed together. Advancement and retraction of the needle 13 and outer sheath 44 is controlled at the proximal end of the catheter, allowing the catheter 10 to be deployed, the needle 13 extended, agent delivered to an injection site in the wall of the patient's body lumen 30, the needle 13 retracted, and the support member arms collapsed for removal or repositioning in the body lumen 30. The outer sheath 44 extends coaxially along the shaft proximal to the support members, and has a proximal end that can be manipulated by the physician to advance or retract the outer sheath 44, optionally using a proximal handle mechanism. The outer sheath can remain on the shaft 11 in the retracted configuration to be used to collapse the deployed arms 20 following an injection, or a different recovery catheter (not shown) can be used to collapse the deployed arms 20 to the low profile configuration for repositioning or removal. The arms 20 collapse as the outer sheath 44 (or recovery catheter) is slidably advanced over at least a proximal section of the arms 20.

Thus, the distal end of the outer sheath 44 (or recovery catheter) can be at, or proximal to, or distal to the distal end of the catheter shaft 11 in the advanced configuration. In the embodiment illustrated in FIG. 5, the distal end of the outer sheath 44 in the advanced configuration is located proximal to the distal end of the arms 20 of the distal support member 16.

The support members each have an annular collar section 24 which is bonded to an outer surface of the shaft tubular member 40, to securely mount the support member to the shaft 11. The collar section 24 preferably extends fully around the circumference of the tubular member 40, although a mounting section extending intermittently or otherwise only partially around the circumference of the tubular member 40 could alternatively be used. The fixed end 21 of each arm is at the distal end of the collar section 24 such that the arms extend distally from the distal end of the collar section 24. The arms and collar section can be formed integrally as a one-piece unit by cutting or otherwise removing material from a tubular stock to form the individual arms 20 extending from the annular collar section 24. Alternatively, the arms 20 can be formed separately from the collar section 24 and then bonded (i.e., at the fixed end) to the collar section to form the support member. The support members are typically formed of a metal such as a nickel-titanium alloy (NITINOL), or stainless steel, and are typically bonded to the shaft by an adhesive. Alternatively, at least the collar section 24 of the support members can be formed of a polymeric material and heat fusion bonded to the underlying shaft 11.

Figure 2:
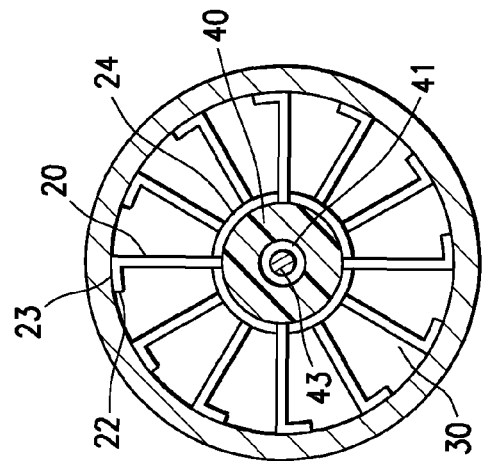
FIGS. 2 and 3 are transverse cross sections of FIG. 1, taken along lines 2-2 and 3-3, respectively.
Figure 3:
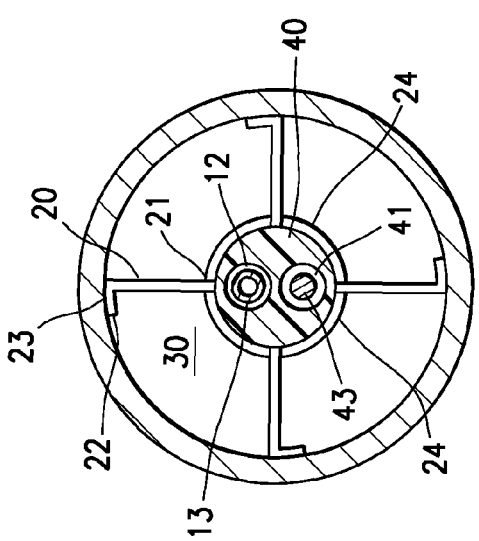
Figure 4:
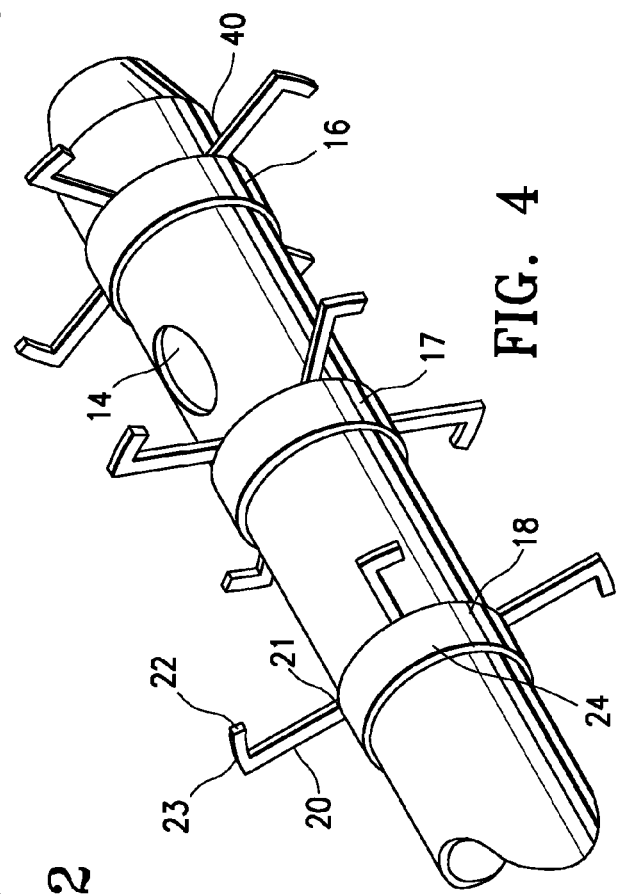
FIG. 4 illustrates a perspective view of the distal shaft section of the catheter of FIG. 1.

In the embodiment of FIG. 1, the opposite end 22 of each arm 20 is a free end bent at a substantially right angle to form the anchor end section 23 of the arm, as best shown in FIGS. 2 and 3 illustrating transverse cross sections of FIG. 1, taken along lines 2-2 and 3-3, respectively, and in FIG. 4 illustrating a perspective view of the distal shaft section of the catheter of FIG. 1. As each arm 20 transforms from the low to the high profile configuration and back again, it pivots through an arc, and the opposite free end 22 of the arm 20 of the embodiment of FIG. 1 is bent in a direction perpendicular, or substantially perpendicular (somewhat greater than or less than 90 degrees), to the arc to form the anchor end section 23. In the embodiment of FIG. 1, the free ends 22 of the support member arms are bent in the same direction (counterclockwise).

The free end 22 and anchor end section 23 are configured to be atraumatic to the wall of the body lumen 30, for example by having rounded (i.e., non-sharp) edges, and by providing a sufficient length to the anchor end section 23 to distribute the force of the arm 20 against the body lumen wall to a greater degree than would be achieved if the arm 20 contacted the body lumen wall just at the free end 22 of the arm 20. The anchor end section 23 in at least one embodiment is configured to contact the wall of the body lumen 30 along all or nearly all of the length of the anchor end section 23 in the high profile configuration to securely support the shaft.

In the embodiment of FIG. 1, each support member 16, 17, 18 has a total of four arms circumferentially spaced around the circumference of the shaft 11. The arms 20 of each support member are preferably radially (i.e., rotationally) misaligned with the arms of at least the adjacent support members, as best shown in FIG. 3. By thus "clocking" the arrangement of the arms, the stabilization and centering of the shaft 11 provided by the deployed arms 20 is improved. Although the embodiment of FIG. 1 has the arms of all three support members radially misaligned with each other, in an alternative embodiment (not shown), the distal support member 16 and the second proximal support member 18 have radially aligned arms around the circumference of the shaft. Although illustrated with four arms each, each support member can have a larger or smaller total number of arms 20, depending upon the catheter size and application and the desired level of stabilization required. Fewer arms 20 provide less support to the shaft, but also provide a corresponding increase in the flexibility of the flexible distal shaft section. Additionally, the outer sheath 44 can be made correspondingly thinner and more flexible for radially restraining and collapsing a smaller number of arms 20.

The length of the longitudinally extending intermediate section of the arm (i.e., between the collar section 24 and the anchor end section 23) is preferably sized to fit the body lumen 30, such that the deployed arms extend in a mainly radial direction (i.e., perpendicular) from the shaft for improved support of the shaft 11 during advancement of the needle 13 into the wall of the body lumen 30. The arms 20 are thus unlike a radially expanding cage formed by a series of connected struts that ramp away from the shaft at an angle relative to a plane perpendicular to the longitudinal axis of the shaft 11. Also unlike a radially expanding cage, the individual arms of the support members of the invention pivot as individual units to form the high profile configuration. This configuration of the support members provides the desired centering and stabilization of the catheter shaft during advancement and retraction of the needle 13, but with minimal increase in the stiffness and size of the low profile configuration of the distal shaft section. Specifically, when the needle contacts the vessel wall, it creates a reactive load on the catheter body, which can force the catheter shaft away from the vessel wall and make it more difficult to puncture the vessel. The stabilization provided by the support member arms 20 is designed to limit this disadvantageous instability of the shaft, to facilitate accurate delivery of the agent to a desired injection site. The collar sections 24 of the distal and proximal support members 16, 17 can be mounted on the shaft directly adjacent to or slightly spaced from the port 14, to provide support to shaft adjacent to the location of the port 14. Typically, the collar sections 24 of the support members are spaced apart from each other by about the length of the intermediate section of the arms 20, such that the arms 20 do not overlap the distally adjacent support member in the collapsed configuration.

The arms are configured to pivot in a distal direction down towards the shaft, to collapse to the low profile configuration as the outer sheath 44 is slidably advanced thereover as illustrated in FIG. 5. FIG. 6 illustrates a transverse cross section of FIG. 5, taken along line 6-6. The arms 20 may be configured such that at least a section thereof is forced down against the outer surface of the underlying section of the shaft tubular member 40, or, alternatively, the support members and outer sheath 44 are be configured such that the arms 20 are slightly spaced away from the outer surface of the underlying section of the shaft tubular member in the low profile collapsed configuration. The arms 20 are placed in the low profile collapsed configuration illustrated in FIG. 5 during the initial advancement of the catheter in the patient's vasculature, and again at the end of a procedure as the arms are re-collapsed after an agent has been delivered through the needle 13 into the wall of the body lumen. In an alternative low profile configuration, the arms can be folded back proximally (i.e., pivot in a proximal direction down towards the shaft) within the outer sheath 44 during the initial advancement). The arms are sufficiently thin and flexible at least at the location of the fixed end 21 to allow the arm itself to flex and bend at the pivot point without requiring a hinge structure at the fixed end 21. Additionally, the arms are preferably formed with a sufficient thickness and of a material that allows the arm to repeatedly pivot to transform repeatedly from the high profile to the collapsed low profile configuration.

Figure 7:
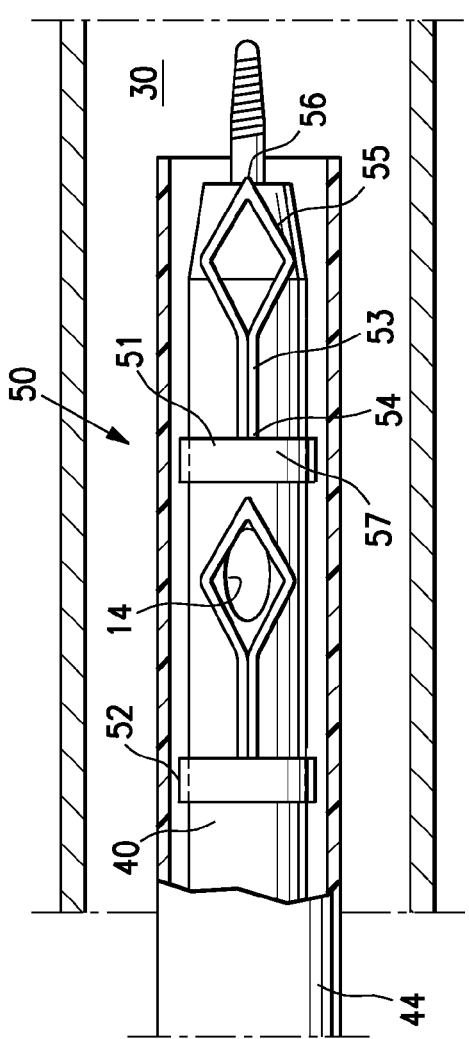
FIG. 7 is an elevational, partially in section, view of a distal shaft section of an alternative agent delivery perfusion catheter embodying features of the invention, in which the support member articulating arms have a diamond shaped anchor end section, with the arms illustrated in the low profile configuration.
Figure 8:
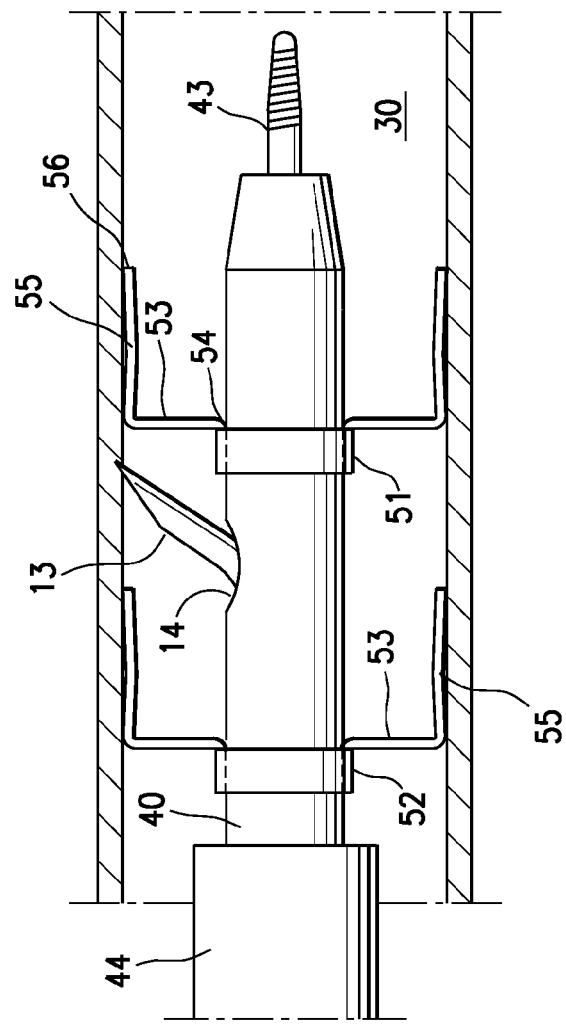
FIG. 8 illustrates the catheter of FIG. 7 with the arms in the high profile configuration.

FIGS. 7 and 8 illustrate an alternative embodiment in which the support member arms have a substantially diamond or kite shaped anchor end section, i.e., a quadrilateral with two distinct pairs of adjacent, congruent (equal length) sides having two internal acute angles and two internal obtuse angles. The catheter 50 is otherwise similar to the catheter 10 of FIG. 1, with the outer sheath 44 illustrated in the advanced configuration in FIG. 7 and in the retracted configuration in FIG. 8. The outer sheath 44 is illustrated in longitudinal cross section in FIG. 7 to show the support members and shaft tubular member 40 therein, and FIG. 8 illustrates an elevational view of the catheter as seen from a view rotated 90 degrees relative to FIG. 7. Specifically, in the embodiment of FIGS. 7 and 8, a distal support member 51 is at a first location distally adjacent to the needle-through port 14, and a proximal support member 52 is at a second location proximally adjacent to the needle-through port 14, and each arm has two articulating arms 53 having a first end 54 fixedly secured relative to the shaft, and has a bifurcation which bends away and then back to an axis of the arm to form a substantially diamond shaped anchor end section 55, and has an opposite end 56 at a tip of the substantially diamond shaped anchor end section not fixedly secured to the shaft. Similar to the embodiment of FIG. 1, each arm 53 is biased to pivot at the fixed end 54 away from the shaft 11 (e.g., shaft tubular member 40) to transform from a low profile configuration to a high profile configuration in which the arm 53 extends laterally away from the shaft 11 and the anchor end section 55 contacts, without piercing, the patient's body lumen wall to support the shaft 11 proximal and distal to the needle-though port 14 in the body lumen 30. Each support member has an annular collar section 57 bonded to the shaft tubular member 40 as in the embodiment of FIG. 1.

The diamond shaped anchor end section 55, unlike the embodiment of FIG. 1, extends distally forward from the intermediate section (i.e., the section between the collar section 57 and anchor end section 55) of the arm 20. In one embodiment, the diamond shaped anchor end section of each arm has an length and a width substantially equal to the length of the arm from the fixedly secured first end to a base of the diamond shaped anchor end section. The diamond shape is preferably configured to provide an arm 53 that more readily flexes providing greater stabilization and less trauma to the portion of the body lumen wall that it contacts in the high profile configuration. Additionally, to further decrease trauma to the vessel, the most radial portions of the support member arms of the catheters of the invention may have a greater radius of curvature. In an alternative embodiment, the anchor end section of the support member articulating arms has a square shape similar to the diamond shape of anchor end section 55 but with four internal right angles. In a square shaped anchor end section, the arm piece bends away at the bifurcation at a substantially right angle relative to arc through which the arm pivots similar to the embodiment of FIG. 1, but unlike the FIG. 1 embodiment, it further extends distally forward of the intermediate section of the arm to form the square shaped anchor end section.

In one embodiment, each arm 53 is configured such that the size and shape of the diamond shaped anchor end section 55 does not have to elongate or otherwise change during the transition of the arm between the low and high profile configurations. In one embodiment, each arm 53 is formed of a single piece, such as a wire secured to the collar section 57, with the anchor end section 55 diamond shape formed by bending a continuous length of the arm wire at four or five points. In the illustrated embodiment, a wire forming the arm 53 extends away from and then back to the annular collar section 57 along itself between the collar section 57 and diamond shaped anchor end section 55, which increases the strength of attachment and force of the arm 53, although the wire can alternatively have an end secured at the bifurcation. Specifically, each arm is formed by a single wire which is doubled over to form a loop, such that the wire has a first axially aligned section, and a bent section forming the diamond shaped anchor end section, and a second axially aligned section which extends side-by-side with the first axially aligned section. The arm 53 can alternatively be formed as an integral one-piece unit with the support member collar section 57, by cutting or otherwise removing material from a tubular stock.

Although the catheter shaft tubular member illustrated in the embodiments of FIGS. 1 and 7 has a dual lumen configuration with a guidewire lumen which slidably receives guidewire 43 therein, it should be understood that a variety of suitable catheter shaft configuration can alternatively be used with a catheter of the invention, including catheter shaft configurations not having a guidewire lumen.

Figure 9:
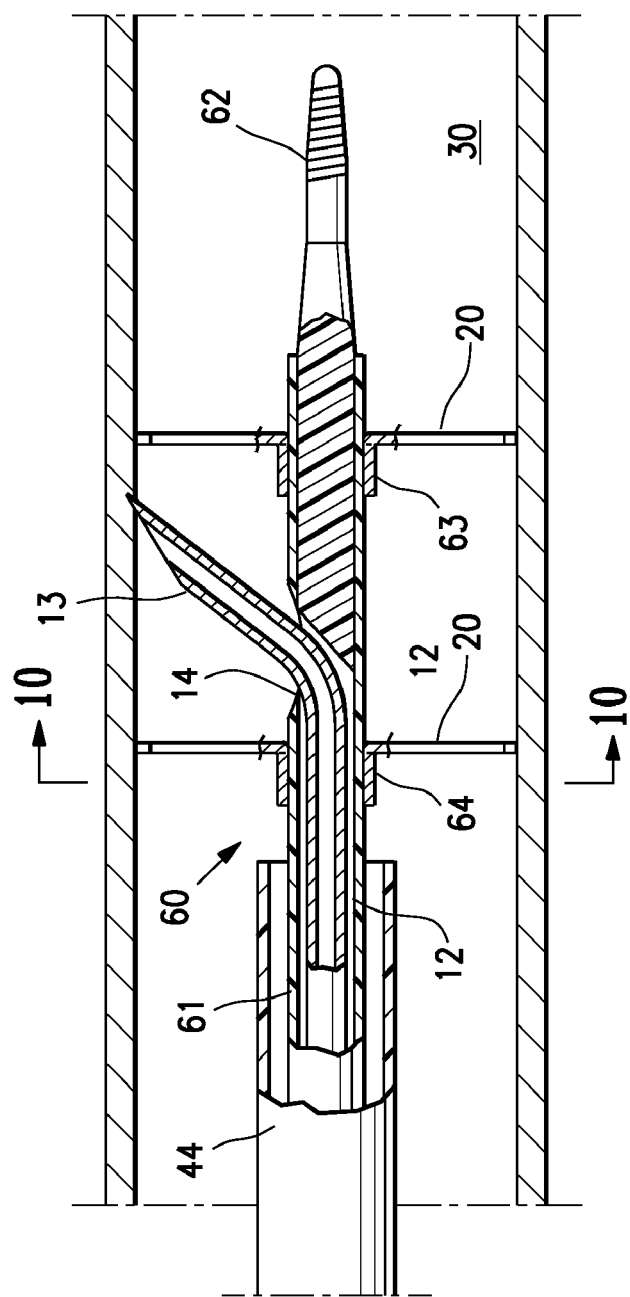
FIG. 9 is an elevational, partially in section, view of a distal shaft section of an alternative agent delivery perfusion catheter embodying features of the invention, in which the catheter is a fixed wire device with the support members mounted on a needle sheath tubular member.
Figure 10:
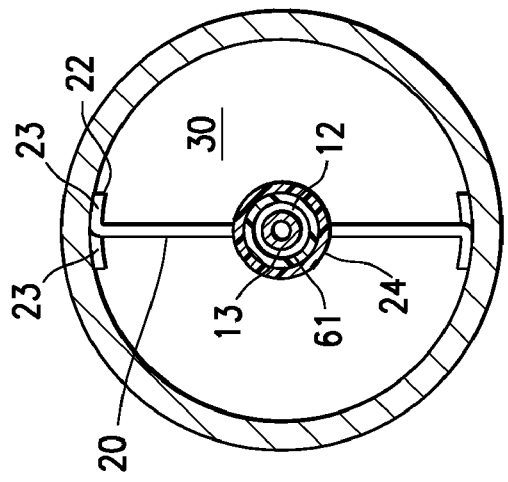
FIG. 10 is a transverse cross section of FIG. 9, taken along line 10-10.

FIG. 9 illustrates a distal section of an alternative catheter 60 embodying features of the invention, in which the catheter shaft consists essentially of a needle sheath tubular member 61 having the needle-through lumen 12 and port 14 therein, and articulating arm support members 63, 64 are mounted to the needle sheath tubular member 61. In the illustrated embodiment, the needle sheath tubular member 61 has a closed distal end with a flexible distal tip coil member 62. The catheter 60 is thus a fixed wire type of catheter with a single lumen, which is not configured to be slidably advanced over a guidewire. A distal support member 63 is distally adjacent to the port 14 and a proximal support member 64 is proximally adjacent to the port 14. The support members have the articulating arms 20 of the embodiment of FIG. 1, with a fixed end, and the free opposite end 22 bent at a substantially right angle to form the anchor end section 23 (see FIG. 10), and the collar section 24 bonded to the outer surface of the shaft needle sheath tubular member 61. As best shown in FIG. 10, illustrating a transverse cross section of FIG. 9 taken along line 10-10, the anchor end sections 23 of the arms of the distal support member 63 are bent in the opposite direction to the arms of the proximal support member 64. Additionally, unlike the embodiment of FIG. 1, the support members 63, 64 each have only two articulating arms, and the arms 20 of the distal support member 63 are radially aligned around the circumference of the shaft with the arm 20 of the proximal support member 64. Alternatively, the two arms 20 of the distal support member 63 could be radially misaligned with the two arms 20 of the proximal support member 64, to provide improved centering of the shaft (i.e., needle sheath tubular member 61), for example, by providing the arms in an X-shaped pattern. Similarly, the number of support members and arms may be increased or decreased as discussed above in relation to the previous embodiments.

In a method of using a catheter of the invention to deliver an agent to an injection site in a wall of a patient's body lumen 30, such as a coronary blood vessel, the catheter is slidably advanced in the patient's vasculature to the desired location in the vessel, in the low profile configuration within the outer sheath 44. The outer sheath may be prepositioned first (i.e., without the catheter therein) at the desired injection site in the blood vessel, or alternatively advanced together with the catheter therein. Once at the desired location in the body lumen, the outer sheath 44 is proximally retracted relative to the support members until its distal end is proximal to the proximal support member, so that the arms of the support members pivot away from the shaft and the anchor end section of each arm contacts the inner surface of the blood vessel wall, thereby providing support and preferably centering the shaft at the desired injection site. The needle 13 is then advanced through the port 14 in the shaft until it penetrates the target tissue of the wall of the blood vessel, and agent is caused to flow through the needle lumen and out the distal tip of the needle from an agent source connected to the proximal end of the catheter. A needle stop (not shown) which sets a limited extended distance for the needle is typically provided in the shaft 11 or as part of a proximal handle mechanism. After the flow of agent is stopped, the needle is proximally retracted into the lumen 12 of the shaft, and the outer sheath 44 is distally advanced over the support members to distal point at which it covers at least a proximal section of the arms of the distal-most support member, to collapse and constrain the arms in the low profile configuration. Following optional additional injections, the outer sheath 44 and catheter may then be removed from the patient to complete the procedure. Alternatively, the arms of the support members can be collapsed and constrained within a separate recovery catheter similar to the outer sheath 44 used to deliver the catheter.

A variety of suitable agents can be delivered using a catheter and method of the invention. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. Suitable therapeutic agents include, but are not limited to, thrombolytic drugs, anti-inflammatory drugs, anti-proliferative drugs, drugs restoring and/or preserving endothelial function, and the like. A variety of bioactive agents can be used including but not limited to peptides, proteins, oligonucleotides, cells, and the like. The agent is typically a therapeutic agent for restenosis, although the agent can be delivered for a variety of treatment procedures, including treatment of a diseased (occluded) blood vessel by delivery of the agent directly to the diseased blood vessel, or treatment of the myocardium of the heart by delivery of an agent to one of the (healthy) coronary arteries. In a presently preferred embodiment, the agent is an anti-inflammatory agent including steroids, or is an agent that induces cholesterol efflux from arterial wall plaque including ApoA1 mimetic peptides, PPARα agonists. In one embodiment, the catheter is used to deliver an agent into organ tissue, such as renal, spleen, liver, or stomach tissue, or any body organ with vasculature that runs near a target treatment site. The agent(s) can be delivered directly into the organ tissue adjacent to a disease. Suitable agents include anti-proliferative, anti-inflammatory, anti-neoplastic, anti-platelet, anti-coagulant, anti-fibrin, anti-thrombotic, anti-mitotic, antibiotic, anti-allergic, and antioxidant compounds. For example, in one embodiment, the catheter is used to deliver therapeutic agent microparticles into renal tissue. Modifications to the catheter device components may be required to produce a device that operates within different organ vascular systems, for example by reducing or enlarging the size of the device for use in body lumens that are smaller or larger relative to typical coronary vessels. In addition to therapeutic agents, a variety of diagnostic agents can be used according to the present invention. The agent may be provided in a variety of suitable formulations and carriers including liposomes, polymerosomes, nanoparticles, microparticles, lipid/polymer micelles, and complexes of agents with lipid and/or polymers, and the like.

The dimensions of catheters 10, 50, 60 depend upon factors such as the catheter type, and the size of the artery or other body lumen through which the catheter must pass. The overall length of the catheter may range from about 100 to about 150 cm.

The shaft tubular members can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. A variety of suitable shaft configurations can be used including one or more of the tubular members formed of single or multiple layers or sections of tubing, as are conventionally known for catheter shaft design The term "catheter" should be understood to refer to a variety of device designs generally having an elongated structure configured for percutaneous advancement through a patient's vasculature. Additionally, although discussed primarily in terms of supporting a catheter shaft at the location of a sidewall port for lateral egress of a needle, the support member could alternatively be provided adjacent to a port in an end of a tubular member of the shaft, such as a distal tip port. While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

I claim:

1. An agent delivery catheter configured for delivering an agent to an injection site in a wall of a patient's body lumen, comprising:
   a) an elongated shaft having a proximal end, a distal end, a needle-through lumen in communication with at least one needle-though port in a distal shaft section; and
   b) a support member mounted to the shaft at a first location longitudinally adjacent to the needle-through port, comprising a plurality of articulating arms, each arm having an end fixedly secured relative to the shaft, and an opposite free end to form an anchor end section of the arm, and the arm is biased to pivot at the fixed end away from the shaft to transform from a low profile configuration to a high profile configuration in which the arm extends substantially perpendicularly away from the shaft and the anchor end section contacts, without piercing, the patient's body lumen wall to support the shaft adjacent to the needle-though port in the body lumen.

2. The catheter of claim 1 wherein the needle-though port is in a side of a distal shaft section for lateral egress of a needle, and the first location of the support member is distally adjacent to the needle-through port such that said support member is a distal support member, and the catheter includes a proximal support member mounted to the shaft at a second location proximally adjacent to the needle-through port comprising a plurality of articulating arms like the distal support member such that each proximal support member arm extends substantially perpendicular away from the shaft in a high profile configuration.

3. The catheter of claim 2 wherein the distal support member has two or more distal articulating arms circumferentially spaced apart at the first location distal to the port, and the proximal support member has two or more proximal articulating arms circumferentially spaced apart at the second location proximal to the port, and each arm is configured to transform from the low to the high profile as an individual unit with an articulating length separate from and not connected to the adjacent arms.

4. The catheter of claim 3 wherein each support member includes a collar section which has the pivoting fixed end of each arm secured thereto, and which has an inner surface secured to the shaft to thereby fixedly secure the support member to the catheter shaft.

5. The catheter of claim 4 wherein the support member collar sections are spaced apart by a length not less than a length of the support member arms.

6. The catheter of claim 3 wherein the arms of the proximal support member are radially misaligned around the circumference of the shaft relative to the arms of the distal support member.

7. The catheter of claim 2 including one or more additional articulating arm support members.

8. The catheter of claim 2 wherein the catheter has a second proximal articulating arm support member, located proximal to the proximal support member.

9. The catheter of claim 8 wherein the proximal support members and the distal support member each have four articulating arms circumferentially spaced apart around the circumference of the shaft such that the arms of adjacent support members are radially misaligned.

10. The catheter of claim 2 wherein the catheter includes an outer sheath slidably disposed on the support members, having an advanced configuration surrounding the support members to constrain the arms in the low profile configuration, and a retracted configuration which allows the arms to pivot to transform to the high profile configuration, and the arms are biased to pivot upon removal of the constraining force of the outer sheath.

11. An agent delivery catheter configured for delivering an agent to an injection site in a wall of a patient's body lumen, comprising:
  a) an elongated shaft having a proximal end, a distal end, a needle-through lumen, and at least one needle-though port in a side of a distal shaft section for lateral egress of a needle; and
  b) a distal support member comprising a plurality of distal articulating arms at a first location distally adjacent to the needle-through port, and a proximal support member having a plurality of proximal articulating arms at a second location proximally adjacent to the needle-through port, and each distal articulating arm and proximal articulating arm has an end fixedly secured relative to the shaft, and has a bifurcation which bends away and then back to an axis of the arm to form a substantially diamond shaped anchor end section, and has an opposite end at a tip of the diamond shaped anchor end section not fixedly secured to the shaft, and is biased to pivot at the fixed end away from the shaft to transform from a low profile configuration to a high profile configuration in which the arm extends substantially perpendicularly away from the shaft and the anchor end section contacts, without piercing, the patient's body lumen wall to support the shaft proximal and distal to the needle-though port in the body lumen.

12. The catheter of claim 11 wherein the distal support member has no more than two distal articulating arms circumferentially spaced apart at the first location distal to the port, and the proximal support member has no more than two proximal articulating arms circumferentially spaced apart at the second location proximal to the port, and each arm is configured to transform from the low to the high profile as an individual unit with an articulating length separate from and not connected to the adjacent arms.

13. The catheter of claim 11 wherein the each arm is formed by a single wire which is doubled over to form a loop, such that the wire has a first axially aligned section, and a bent section forming the diamond shaped anchor end section, and a second axially aligned section which extends side-by-side with the first axially aligned section.

14. The catheter of claim 11 wherein each support member includes an annular collar section which has the pivoting first end of each arm secured thereto, and which has an inner surface secured to the shaft to thereby fixedly secure the support member to the catheter shaft.

15. The catheter of claim 11 wherein the catheter includes an outer sheath slidably disposed on the support members, having an advanced configuration surrounding the support members to constrain the arms in the low profile configuration, and a retracted configuration which allows the arms to pivot to transform to the high profile configuration, and the arms are biased to pivot upon removal of the constraining force of the outer sheath.

16. An agent delivery catheter configured for delivering an agent to an injection site in a wall of a patient's body lumen, comprising:
  a) an elongated shaft having a proximal end, a distal end, a needle-through lumen in communication with at least one needle-though port in a distal shaft section;
  b) a distal support member mounted to the shaft at a first location longitudinally adjacent to the needle-through port, comprising a plurality of articulating arms;
  c) a proximal support member mounted to the shaft at a second location longitudinally adjacent to the needle-through port, comprising a plurality of articulating arms, wherein each arm of the distal support member and proximal support member has an end fixedly secured relative to the shaft, and an opposite free end which forms an anchor end section of the arm, each arm being biased to pivot at the fixed end away from the shaft to transform from a low profile configuration to a high profile configuration in which the arm extends substantially perpendicularly away from the shaft and the anchor end section contacts, without piercing, the patient's body lumen wall to support the shaft adjacent to the needle-though port in the body lumen; and
  d) an outer sheath slidably disposed on the distal and proximal support members, having an advanced configuration surrounding the support members to constrain the arms of each support member in the low profile configuration, and a retracted configuration which allows the arms to pivot to transform to the high profile configuration, and the arms are biased to pivot upon removal of the constraining force of the outer sheath.

* * * * *